US009930906B1

(12) United States Patent
Horler et al.

(10) Patent No.: US 9,930,906 B1
(45) Date of Patent: Apr. 3, 2018

(54) PROTEIN BEVERAGES

(71) Applicant: Swallow Solutions, LLC, Madison, WI (US)

(72) Inventors: Eric Horler, Madison, WI (US); Jacqueline Hind, Madison, WI (US); JoAnne Robbins, Madison, WI (US); Elfi Anggreani, Madison, WI (US); Marcus Brody, Madison, WI (US); Malcond Valladares, Madison, WI (US); Eric James, Madison, WI (US)

(73) Assignee: SWALLOW SOLUTIONS, LLC, Madison, WI (US)

( * ) Notice: Subject to any disclaimer, the term of this patent is extended or adjusted under 35 U.S.C. 154(b) by 0 days.

(21) Appl. No.: 15/588,224

(22) Filed: May 5, 2017

(51) Int. Cl.
*A23L 2/66* (2006.01)
*A23L 2/44* (2006.01)
*A23L 2/60* (2006.01)
*A23L 2/56* (2006.01)
*A23L 2/52* (2006.01)

(52) U.S. Cl.
CPC .................. *A23L 2/66* (2013.01); *A23L 2/44* (2013.01); *A23L 2/52* (2013.01); *A23L 2/56* (2013.01); *A23L 2/60* (2013.01); *A23V 2002/00* (2013.01)

(58) Field of Classification Search
CPC ........................................................ A23L 2/66
See application file for complete search history.

(56) References Cited

U.S. PATENT DOCUMENTS

| | | | | |
|---|---|---|---|---|
| 4,835,002 A | * | 5/1989 | Wolf | A23L 2/38 426/590 |
| 5,641,531 A | * | 6/1997 | Liebrecht | A23G 9/40 426/583 |
| 6,106,874 A | * | 8/2000 | Liebrecht | A23L 2/02 426/583 |
| 6,475,539 B1 | * | 11/2002 | DeWille | A23L 2/38 426/573 |
| 2003/0099753 A1 | * | 5/2003 | Yang | A23L 2/02 426/599 |
| 2008/0206415 A1 | * | 8/2008 | Sherwood | A23J 3/08 426/326 |
| 2011/0256272 A1 | * | 10/2011 | Johns | A23L 2/52 426/112 |
| 2011/0305799 A1 | * | 12/2011 | DeWille | A23L 2/52 426/73 |
| 2013/0243904 A1 | * | 9/2013 | Cordle | A23L 1/296 426/2 |
| 2014/0004045 A1 | | 1/2014 | Mendenhall et al. | |
| 2014/0212565 A1 | * | 7/2014 | Bradley | A23L 2/56 426/580 |

OTHER PUBLICATIONS

Nordic Sugar, "The functional properties of sugar on a technical level". Available online from nordicsugar.com as of Oct. 21, 2012. pp. 1-56. (Year: 2012).*
"Markets Ripe for New Product Developments, and Hydrocolloids". Available online from cpkelco.com as of Jun. 6, 2015. pp. 1-4. ( Year: 2015).*
Flavour Creations Pre-Thickened Ready to Drink Pro Lemon Lime and Caramel. Available online as of Mar. 5, 2016 from www.flavourcreations.com.au. pp. 1-2. (Year: 2016).*
Ghosh et al., "Polysaccharide-Protein Interactions and Their Relevance in Food Colloids" Intech Open Access Publisher; 201, p. 396-408, (2012).
Khezri et al., "The Effect of Xanthan Gum and Temperature on Foam Stability of Milk-Based Espresso Coffees" Journal of Food Biosciences and Technology 2017, 7:15-22.

* cited by examiner

*Primary Examiner* — Jenna A Watts
(74) *Attorney, Agent, or Firm* — Casimir Jones, S.C.

(57) ABSTRACT

Provided herein are protein beverages. In particular, provided herein are protein beverages that are thickened, stable, and ready to drink beverages designed for consumption by subjects (e.g., subjects having a need for thickened beverages). In some embodiments, the subjects are subjects having dysphagia.

18 Claims, No Drawings

PROTEIN BEVERAGES

FIELD

Provided herein are protein beverages. In particular, provided herein are protein beverages that are thickened, stable, and ready to drink beverages designed for consumption by subjects (e.g., subjects having a need for thickened beverages). In some embodiments, the subjects are subjects having dysphagia.

BACKGROUND

Dysphagia, the medical term for difficulty in swallowing, affects more than 18 million adults and millions more children in the U.S. Dysphagia is associated with increased mortality and morbidity. Patients with dysphagia suffer from many chronic problems including dehydration, pulmonary complications, reduced quality of life, and malnutrition. Sarcopenia, the age-related loss of muscle mass, is a primary cause of dysphagia and is exacerbated by malnutrition. Malnutrition-Sarcopenia syndrome is a chronic affliction among older adults, resulting of their decreased swallowing function. In addition to age-related sarcopenia, muscle weakness leading to dysphagia can be caused by other health problems such as stroke, neurodegenerative diseases, and cancer. One of the most common treatment strategies for dysphagia is drinking dietary beverages that are thickened. Although muscle weakness can be attenuated with adequate protein intake, current thickened dietary beverages for dysphagia primarily provide carbohydrates and contain little or no protein.

What is needed are dietary beverages for dysphagia that provide protein.

SUMMARY

Provided herein are protein beverages. In particular, provided herein are protein beverages that are thickened, stable, and ready to drink beverages designed for consumption by subjects (e.g., subjects having a need for thickened beverages). In some embodiments, the subjects are subjects having dysphagia.

The beverages described herein meet an unmet need of providing a beverage that is of the proper viscosity and turbidity for use in individuals with swallowing disorders (e.g., having dysphagia), or individuals without swallowing disorders, and providing suitable levels of protein and calories. The beverages described herein are useful, for example, in preventing aspiration and treating dehydration and malnutrition.

For example, in some embodiments, provided herein is a beverage, comprising: 2 to 10 g of complete protein per 100 g or 100 mL serving, wherein the beverage has an apparent viscosity between 50 cp and 2000 cp. In some embodiments, the beverage is clear (e.g., a turbidity reading from 0 to 1000 NTUs). In some embodiments, the protein is hydrolyzed protein. In some embodiments, the protein is complete protein. In some embodiments, the protein is hydrolyzed and complete protein. In some embodiments, the protein has a protein digestibility-corrected amino acid score (PDCAAS)>0.9 (e.g., greater than 0.9, 1.0, 1.1, 1.2, 1.3, 1.4, or 1.5). In some embodiments, the beverage has approximately (+/−10%) 100 kcals of energy per 100 g or 100 mL of beverage or more (e.g., 110, 120, 130, 150 or more).

In some embodiments, the beverage is provided as ready-to-drink (i.e., no additional ingredients or processing is required before consumption, such as addition of a thickening agent). In some embodiments, the beverage is shelf stable at room temperature (e.g., for 1 day, 1 week, 1 month, 6 months, or 1 year or more). In some embodiments, the beverage is provided frozen (e.g., in a cup or another format (e.g., on a stick)) and either thawed prior to consumption or consumed frozen, with melting occurring in the mouth or digestive tract.

In some embodiments, the beverage has one or more or each of the following characteristics or properties: 2 to 10 g of complete protein per 100 mL serving, an apparent viscosity between 50 cp and 2000 cp, clear (e.g., a turbidity reading from 0 to 1000 NTUs), ready to drink format, and approximately 100 kcals of energy per 100 g or 100 mL of beverage.

In some embodiments, beverage comprises or consists of one or more or each of water, a protein source, a carbohydrate source, a thickener (e.g., gum), a salt, an acid, a preservative, flavoring, and coloring. In some embodiments, the beverage comprises or consists of a protein source and a gum. In some embodiments, the beverage comprises or consists of a protein source, a gum and an acid. In some embodiments, the beverage comprises or consists of a protein source, a gum, and a preservative. In some embodiments, the beverage comprises of consists of a protein source, a gum, and an acid. In some embodiments, the beverage comprises or consists of a protein source, a gum, and a salt. In some embodiments, the beverage comprises or consists of a protein source, a gum, a salt, and an acid. In some embodiments, the beverage comprises or consists of a protein hydrolysate (e.g., whey protein hydrolysate) and a gum. In some embodiments, the beverage comprises or consists of a protein hydrolysate, a gum, and an acid. In some embodiments, the beverage comprises or consists of a protein hydrolysate, a gum, and a preservative. In some embodiments, the beverage comprises or consists of a protein hydrolysate, a gum, and an acid. In some embodiments, the beverage comprises or consists of a protein hydrolysate, a gum, and a salt. In some embodiments, the beverage comprises or consists of a protein hydrolysate, a gum, a salt, and an acid. In some embodiments, the thickener is not a starch (e.g., not corn starch). In some embodiments, the beverage does not contain a starch (e.g., does not contain corn starch). In some embodiments, the flavoring is a juice flavoring or a juice-like flavoring. In some embodiments, the beverage has a pH of less than 4.5 (e.g., less than 4.5, 4.0, 3.5, 3.0, or 2.0). In some embodiments, the beverage has a pH of 2-8 (e.g., 2-7, 2-6, 2-5, 2-4, 2-3, 3-7, 3-6, 3-5, 3-4, 4-7, 4-6, 4-5, etc).

In some embodiments, the beverage further comprises or consists of one or more or each of: one or more gums, a sweetener, an acid, a preservative, or one or more coloring or flavoring agents. In some embodiments, the gum is cellulose gum and/or xanthan gum. In some embodiments, the beverage comprises or consists of one or more or each of xanthan gum, cellulose gum, whey protein hydrolysate, ascorbic acid, citric acid, malic acid, sodium benzoate, sodium citrate, sugar, phosphoric acid, and water. In some embodiments, the whey protein hydrolysate is present at a concentration of 6% to 7% w/w (e.g., 6.3% or 6.6%).

The present disclosure is not limited to specific formulations of beverages. Exemplary formulations include, but are not limited to, those disclosed below. In the exemplary beverages below, all amounts are in % w/w, unless specified otherwise.

For example, in some embodiments, the beverage comprises or consists of one or more or each of water, whey protein hydrolysate, flavoring, coloring, citric acid, malic acid, sodium benzoate, sugar, phosphoric acid, xanthan gum, and cellulose gum (e.g., 72.6% water, 6.6% whey protein hydrolysate, 0.65% flavoring, 0.13% coloring, 0.07% citric acid, 0.035% malic acid, 0.025% sodium benzoate, 18.2% sugar, 0.66% phosphoric acid, 0.3% xanthan gum, and 0.82% cellulose gum). In some embodiments, the beverage comprises or consists of one or more or each of water, whey protein hydrolysate, ascorbic acid, flavoring, coloring, citric acid, malic acid, sodium benzoate, sugar, phosphoric acid, xanthan gum, and cellulose gum (e.g., 72.1% water, 6.3% whey protein hydrolysate, 0.05% ascorbic acid, 0.57% flavoring, 0.13% coloring, 0.07% citric acid, 0.035% malic acid, 0.025% sodium benzoate, 18.7% sugar, 0.66% phosphoric acid, 0.4% xanthan gum, and 1.1% cellulose gum). In further embodiments, the beverage comprises or consists of one or more or each of guar gum, water, whey protein hydrolysate, ascorbic acid, flavoring, coloring, citric acid, malic acid, sodium benzoate, sodium citrate, sugar, and phosphoric acid (e.g., 0.91% guar gum, 72.6% water, 6.6% whey protein hydrolysate, 0.05% ascorbic acid, 0.5% flavoring, 0.013% coloring, 0.07% citric acid, 0.035% malic acid, 0.025% sodium benzoate, 0.04% sodium citrate, 18.5% sugar, and 0.66% phosphoric acid). In other embodiments, the beverage comprises or consists of one or more or each of water, whey protein hydrolysate, ascorbic acid, flavoring, coloring, citric acid, malic acid, sodium benzoate, sodium citrate, sugar, phosphoric acid, xanthan gum, and cellulose gum (e.g., 73.3% water, 6.6% whey protein hydrolysate, 0.05% ascorbic acid, 0.5% flavoring, 0.013% coloring, 0.0% citric acid, 0.035% malic acid, 0.025% sodium benzoate, 0.04% sodium citrate, 18.2% sugar, 0.66% phosphoric acid, 0.45% xanthan gum, and 0.06% cellulose gum). In still further embodiments, the beverage comprises or consists of one or more or each of water, whey protein hydrolysate, ascorbic acid, flavoring, coloring, citric acid, malic acid, sodium benzoate, sugar, and phosphoric acid, xanthan gum, and cellulose gum (e.g., 72.5% water, 6.6% whey protein hydrolysate, 0.05% ascorbic acid, 0.65% flavoring, 0.013% coloring, 0.07% citric acid, 0.035% malic acid, 0.025% sodium benzoate, 18.2% sugar, 0.66% phosphoric acid, 0.33% xanthan gum, 0.91% and cellulose gum). In some embodiments, the present disclosure provides a beverage, comprising or consisting of: water, whey protein hydrolysate, phosphoric acid, flavoring, coloring, citric acid, sodium benzoate, sugar, xanthan gum, cellulose gum, and ethanol (e.g., 71.3% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 2.1% of 95% ethanol; 70.3% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 3.2% of 95% ethanol; or 68.2% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 5.3% of 95% ethanol). In some embodiments, the beverage comprises or consists of xanthan gum, cellulose gum, water, whey protein hydrolysate, flavoring, coloring, sodium benzoate, sugar, and phosphoric acid, (e.g., 73.4% water, 6.5% whey protein hydrolysate, 0.36% flavoring, 0.25% coloring, 0.025% sodium benzoate, 18% sugar, 1.0% of 75% phosphoric acid, 0.38% xanthan gum, and 0.06% cellulose gum). In some embodiments, the beverage comprises or consists of xanthan gum, cellulose gum, water, whey protein hydrolysate, flavoring, coloring, sodium benzoate, sugar, dextrin, citric acid, and phosphoric acid, (e.g., 72.1% water, 6.5% whey protein hydrolysate, 0.7% flavoring, 0.03% coloring, 0.025% sodium benzoate, 18% sugar, 1% dextrin, 0.2% citric acid, 1.0% of 75% phosphoric acid, 0.38% xanthan gum, and 0.06% cellulose gum). In some embodiments, the beverage comprises or consists of xanthan gum, cellulose gum, water, whey protein hydrolysate, flavoring, coloring, sodium benzoate, sugar, citric acid, and phosphoric acid, (e.g., 73.3% water, 6.5% whey protein hydrolysate, 0.55% flavoring, 0.3% coloring, 0.025% sodium benzoate, 18% sugar, 0.2% citric acid, 1.0% of 75% phosphoric acid, 0.38% xanthan gum, and 0.06% cellulose gum)

In further embodiments, the present disclosure provides a method of providing (e.g., delivering and/or administering) a beverage to a subject. In some embodiments, the subject has dysphagia. In some embodiments, the subject is at risk of, is suspected of having, or has one or more conditions selected from, for example, aspiration on thin liquids, dehydration, or malnutrition. In some embodiments, the subject is elderly (e.g., age 65, 70, 75, 80, 85, 90, 95, or older).

In some embodiments, the beverage further comprises one or more of ethanol, medical grade marijuana or a component thereof (e.g., a cannabidiol oil), or synthetic cannabinoids (e.g., dronabinol or nabilone). In some embodiments, the concentration of the medical grade marijuana or a component thereof or synthetic cannabinoid is sufficient to elicit an effect in the subject, including, but not limited to, pain relief, glaucoma treatment, muscle spasm relief, nausea relief, increase in appetite, seizure management, Crohn's disease treatment, and anxiety reduction.

Additional embodiments provide a method of treating dysphagia, comprising: administering a beverage as described herein to a subject in need thereof.

Certain embodiments provide the use of a beverage as described herein to treat dysphagia in a subject.

Other embodiments provide a kit, comprising: a) at least one beverage as described herein; and b) a container for storing and/or providing (e.g., administering) the beverage to a user. In some embodiments, the beverage is packaged in bottles (e.g., plastic or glass bottles with screw top or other lids), plastic cups (e.g., with foil-top or paper-top seals), stick or other support, or other suitable container.

Additional embodiments are described herein.

Definitions

As used herein, the term w/w (weight/weight) refers to the amount of a given substance in a composition on weight basis. For example, a composition comprising 50% w/w phospholipids means that the mass of the phospholipids is 50% of the total mass of the composition (e.g., 50 grams of phospholipids in 100 grams of the composition, such as an oil).

As used herein, the terms "food" and "food products" refer to products and ingredients thereof, taken by the mouth, the constituents of which are active in and/or absorbed by the G.I. tract with the purpose of nourishment of the body and its tissues, refreshment and indulgence. Examples of foods and food and beverage products include, but are not limited to, tea; spreads; ice cream; frozen fruits and vegetables; snacks including diet foods and beverages; condiments; and culinary aids. In some embodiments, a "food" is a material comprising protein, carbohydrate and/or fat, which is used in the body of an organism to sustain growth, repair and vital processes and to furnish energy.

Foods may also contain supplementary substances such as minerals, vitamins and condiments.

As used herein a "food additive" (e.g., as defined by the FDA in 21 C.P.R. 170.3 (e)(l)) includes direct and indirect additives.

As used herein, a "dietary supplement" is a product that is intended to supplement a diet.

As used herein, "complete protein" refers to a source of protein that contains an adequate proportion of all nine of the essential amino acids necessary for the dietary needs of humans or other animals (tryptophan, threonine, isoleucine, leucine, lysine, methionine plus cysteine, phenylalanine plus tyrosine, valine, and histidine). Example of sources of complete proteins include, but are not limited to, meat, poultry, fish, eggs, milk, cheese, yogurt, quinoa, or soybean.

DETAILED DESCRIPTION

Provided herein are protein beverages. In particular, provided herein are protein beverages that are thickened, stable, and ready to drink beverages designed for consumption by subjects (e.g., subjects having a need for thickened beverages). In some embodiments, the subjects are subjects having dysphagia.

Experiments conducted during the course of development of embodiments of the present disclosure resulted in identification and optimization of a number of parameters that provide useful protein beverages. For example, it was experimentally determined that intact proteins, with or without gums and protein protection agents, did not result in a beverage with suitable clarity, viscosity, and heat stability. Thus, beverages that utilize hydrolysed proteins were developed. Further experiments determined that beverages comprising apple juice or Konjac gum were typically not suitable. The balancing of multiple factors, the adjustment of one or which can negatively impact others, makes the identification of suitable or desirable protein beverages a significant challenge. Exemplary problems that arose when selecting ingredients and formulation include protein precipitation, product gelling, and under delivery of protein.

Preferred beverages provide one or more or each of 2 to 10 g of complete (e.g., and hydrolyzed) protein per 100 mL serving, an apparent viscosity between 50 cp and 2000 cp, clear (e.g., a turbidity reading from 0 to 1000 NTUs), ready to drink format, approximately 100 kcals of energy per 100 g or 100 mL of beverage, and suitable palatability (e.g., flavor, mouth feel, etc.).

Exemplary compositions and methods are described below.

I. Compositions

Provided herein is a protein beverage with optimized viscosity and turbidity for use by subjects, for example, with swallowing disorders such as dysphagia.

The beverages are not limited to particular sources of proteins. As described above, in some embodiments, hydrolysed proteins are used to provide superior properties. Protein hydrolysates are a mixture of smaller peptide fragments or free amino acids that results when intact proteins are digested in vitro with enzymes. The industrial process is similar to the natural enzymatic hydrolysis of proteins that takes place in the gastrointestinal system during digestion of a protein meal. Hydrolyzed proteins are often more easily digested and absorbed compared to intact protein and free amino acids and can have reduced allergenic potential compared to intact proteins.

Hydrolyzed whey dairy proteins, whey and casein, and hydrolyzed collagen are the most commonly used hydrolyzed proteins, although the present disclosure is not limited to dairy proteins. For example, in some embodiments, hydrolyzed soy, or collagen plus amino acids are utilized.

In some embodiments, the beverages of the present disclosure comprise up to 10% (e.g., 2 to 10 g of complete protein per 100 mL serving), although other concentrations are specifically contemplated. In some embodiments, the whey protein hydrolysate is present at a concentration of 6% to 7% w/w (e.g., 6.3% or 6.6%).

In some embodiments, the beverage comprises one or more gums. The present disclosure is not limited to particular gums. Examples include, but are not limited to, cellulose gum, guar gum, xanthan gum, or a combination thereof. In some embodiments, gums are present in the beverage at a concentration of 0.1 to 2% (e.g., 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.75, 1.8%, 1.9%, 2%, or a fraction thereof).

In some embodiments, the beverage comprises one or more acids or salts. Examples include, but are not limited to, ascorbic acid, citric acid, malic acid, sodium benzoate, sodium citrate, or phosphoric acid. In some embodiments, acids and/or salts are present in the beverage at a concentration of 0.01 to 1% (e.g., 0.01%, 0.05%, 0.1%, 0.5%, 1.0%, or a fraction thereof).

In some embodiments, the beverage comprises a simple or complex carbohydrate. Examples include, but are not limited to, sucrose, glucose, fructose, honey, maple syrup, etc. In some embodiments, the beverage comprises 10-30% (e.g., 10%, 12%, 14%, 16%, 18%, 20%, 25%, 30%, or a fraction thereof) of carbohydrate.

In some embodiments, the beverage further comprises one or more flavorings, coloring agents, or flavor modulators (e.g., modulone). A variety of such agents are commercially available and are suitable for use in the described beverages (e.g., available from Firmenich (Geneva, Switzerland), Sethness (Skokie, Ill.), Wild (Erlanger, Ky.), or other companies.

The beverages described herein provide at least a portion of an individual's daily caloric needs. In some embodiments, the beverage has 50-200 (e.g., 50, 100, 15, 200, or values therein between) kcals of energy per 100 g or 100 mL of beverage.

The beverages described herein provide a beverage with a viscosity suitable for consumption by individual with swallowing disorders (e.g., having dysphagia). For example, in some embodiments, the beverage has an apparent viscosity between 50 cp and 2000 cp (e.g., 50 cp, 100 cp, 200 cp, 300 cp, 400 cp, 500 cp, 1000 cp, 1500 cp, 2000 cp, or a fraction thereof). Exemplary methods for measuring viscosity are described below.

In some embodiments, the beverage is clear (e.g., a turbidity reading from 0 to 1000 NTUs (e.g., less than, 1000, 500, 200, 100, 50, or 10 NTUs)).

The present disclosure is not limited to specific formulations of beverages. Exemplary formulations include, but are not limited to, those disclosed below. All amounts are given in % w/w, unless specified otherwise. For example, in some embodiments, the beverage comprises water, whey protein hydrolysate, flavoring, coloring, citric acid, malic acid, sodium benzoate, sugar, phosphoric acid, xanthan gum, and cellulose gum (e.g., 72.6% water, 6.6% whey protein hydrolysate, 0.65% flavoring, 0.13% coloring, 0.07% citric acid, 0.035% malic acid, 0.025% sodium benzoate, 18.2% sugar, 0.66% phosphoric acid, 0.3% xanthan gum, and 0.82% cellulose gum). In some embodiments, the beverage comprises water, whey protein hydrolysate, ascorbic acid, flavoring, coloring, citric acid, malic acid, sodium benzoate, sugar, phosphoric acid, xanthan gum, and cellulose gum (e.g., 72.1% water, 6.3% whey protein hydrolysate, 0.05% ascorbic acid, 0.57% flavoring, 0.13% coloring, 0.07% citric acid, 0.035% malic acid, 0.025% sodium benzoate, 18.7% sugar, 0.66% phosphoric acid, 0.4% xanthan gum, and 1.1% cellulose gum). In further embodiments, the beverage comprises guar gum, water, whey protein hydrolysate, ascorbic acid, flavoring, coloring, citric acid, malic acid, sodium benzoate, sodium citrate, sugar, and phosphoric acid (e.g., 0.91% guar gum, 72.6% water, 6.6% whey protein hydrolysate, 0.05% ascorbic acid, 0.5% flavoring, 0.013% coloring, 0.07% citric acid, 0.035% malic acid, 0.025% sodium benzoate, 0.04% sodium citrate, 18.5% sugar, and 0.66% phosphoric acid). In other embodiments, the beverage comprises water, whey protein hydrolysate, ascorbic acid, flavoring, coloring, citric acid, malic acid, sodium benzoate, sodium citrate, sugar, phosphoric acid, xanthan gum, and cellulose gum (e.g., 73.3% water, 6.6% whey protein hydrolysate, 0.05% ascorbic acid, 0.5% flavoring, 0.013% coloring, 0.0% citric acid, 0.035% malic acid, 0.025% sodium benzoate, 0.04% sodium citrate, 18.2% sugar, 0.66% phosphoric acid, 0.45% xanthan gum, and 0.06% cellulose gum). In still further embodiments, the beverage comprises water, whey protein hydrolysate, ascorbic acid, flavoring, coloring, citric acid, malic acid, sodium benzoate, sugar, and phosphoric acid, xanthan gum, and cellulose gum (e.g., 72.5% water, 6.6% whey protein hydrolysate, 0.05% ascorbic acid, 0.65% flavoring, 0.013% coloring, 0.07% citric acid, 0.035% malic acid, 0.025% sodium benzoate, 18.2% sugar, 0.66% phosphoric acid, 0.33% xanthan gum, 0.91% and cellulose gum). In some embodiments, the beverage comprises water, whey protein hydrolysate, phosphoric acid, flavoring, coloring, citric acid, sodium benzoate, sugar, xanthan gum, cellulose gum, and ethanol (e.g., 71.3% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 2.1% of 95% ethanol; 70.3% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 3.2% of 95% ethanol; or 68.2% water, 6.5% whey protein hydrolysate, 0.83% of 75% phosphoric acid, 0.25% flavoring, 0.3% coloring, 0.2% citric acid, 0.025% sodium benzoate, 18% sugar, 0.38% xanthan gum, 0.06% cellulose gum, and 5.3% of 95% ethanol). In some embodiments, the beverage comprises xanthan gum, cellulose gum, water, whey protein hydrolysate, flavoring, coloring, sodium benzoate, sugar, and phosphoric acid, (e.g., 73.4% water, 6.5% whey protein hydrolysate, 0.36% flavoring, 0.25% coloring, 0.025% sodium benzoate, 18% sugar, 1.0% of 75% phosphoric acid, 0.38% xanthan gum, and 0.06% cellulose gum). In the beverage comprises xanthan gum, cellulose gum, water, whey protein hydrolysate, flavoring, coloring, sodium benzoate, sugar, dextrin, citric acid, and phosphoric acid, (e.g., 72.1% water, 6.5% whey protein hydrolysate, 0.7% flavoring, 0.03% coloring, 0.025% sodium benzoate, 18% sugar, 1% dextrin, 0.2% citric acid, 1.0% of 75% phosphoric acid, 0.38% xanthan gum, and 0.06% cellulose gum). In some embodiments, the beverage comprises xanthan gum, cellulose gum, water, whey protein hydrolysate, flavoring, coloring, sodium benzoate, sugar, citric acid, and phosphoric acid, (e.g., 73.3% water, 6.5% whey protein hydrolysate, 0.55% flavoring, 0.3% coloring, 0.025% sodium benzoate, 18% sugar, 0.2% citric acid, 1.0% of 75% phosphoric acid, 0.38% xanthan gum, and 0.06% cellulose gum)

In some embodiments, the beverage further comprises one or more of ethanol, medical grade marijuana or a component thereof (e.g., cannabidiol oil), or synthetic cannabinoids (e.g., dronabinol or nabilone).

In some embodiments, beverages are provided as a thickened liquid or frozen product (e.g., shake, on a stick or other support, cup, etc.).

The beverages described herein are manufactured using any suitable method. Exemplary manufacturing methods are described below.

In some embodiments, hydrolyzed proteins are first blended with water in a stainless-steel tank with constant agitation. Sodium Benzoate is added to the protein solution, followed by a dry blend of one or more acids.

After the acids and salts are completely dissolved in the protein solution, the flavor/color blend is added to the protein solution. The pH is adjusted in steps with 85% phosphoric acid until the solution reaches a pH=3.9. The gums are then dispersed in sucrose and added to the protein solution with high shear mixing.

In some embodiments, solutions are sterilized using high-temperature, short-time pasteurization (HTST, also known as "flash") or ultra-heat-treating (UHT). In some embodiments, commercially available (e.g., from MicroThermics, Inc., Raleigh, N.C.) sterilizers are used. In some embodiments, sterilized beverages are packaged using aseptic processing or hot fill. In some embodiments, the pH is adjusted to neutral when aseptic packaging is used. Beverages (room temperature or frozen) are packaged in any suitable container. Examples include, but are not limited to, bottles (e.g., screw-top plastic bottles or glass bottles), cups (e.g., with paper or foil lids), stick or other support, etc.

In some embodiments, large scale, high throughput manufacturing is utilized.

In some embodiments, beverages are selected to have desirable consumer palatability. Such beverages may be selected using taste-testing experiments for one or more parameters (e.g., including but not limited to, refreshing ("not at all" to "very"), flavor strength, texture, sweetness, smoothness, bitterness, off-flavor, chalkiness, amount of aftertaste, pleasantness of aftertaste, thirst quenching, or mouth coating). In some embodiments, such testing parameters are used to optimize beverage components.

II. Uses

The beverages described herein find use in a variety of applications. In some embodiments, the beverages are specifically used as a source of hydration and nutrition in subjects with swallowing disorders (e.g., having dysphagia). In some embodiments, subjects are elderly (e.g., older than 65) or not elderly. In some embodiments, the use of one or more servings of the described beverages treats or prevents one or more complications of a swallowing disorder (e.g., including, but not limited to, aspiration on thin liquids, dehydration, or malnutrition). In some embodiments, one or more beverages are administered on a daily basis or as needed.

Beverages can be stored, shipped, and/or provided to end users (e.g., subjects) in any suitable containers. In some embodiments, hot fill and aseptic packaging is employed. In some embodiments, the pH of the material is adjusted to neutral or near neutral and supplied in aseptic packaging. In some embodiments, the beverage is stored at room temperature after preparation. In some embodiments, beverages descried herein avoid cold supply chain requirements, which results in a cost savings.

EXPERIMENTAL

Example 1

Methods

This example describes analysis methods used to formulate and characterize exemplary protein beverages.

Rheologic Measurements

Viscosity

Brookfield DV3T controlled stress rheometers, models RV and HA, a water jacketed small sample adapter (SSA), cylindrical sample chamber (Brookfield with defined geometry system for accurate viscosity measurements of small sample volumes in the order of 2 to 16 mL at precise shear rates, jacketed small sample adapter with circulating water pump, and 118 ml vials that were 45 mm in diameter (item #0741-07, SKS Science) were used.

Flow behavior of the samples was measured using two Brookfield DV3T controlled stress rheometers, models RV and HA fitted with temperature controlled small sample adapters and spindle SC4-21 (Brookfield Engineering, Middleboro, Mass.).

Samples with viscosity ranges below 500 cP were measured using model RV, samples with viscosity above 500 cP were measured using model HA.

Samples (7 ml) were loaded using a 10 ml syringe (item #9300-04, SKS Science, West Watervliet N.Y.) and allowed to rest for 3 minutes prior to testing in order to allow for temperature equilibration. Samples were the pre-sheared at 30 s-1 for 3 minutes. A stepped shear test was then run from 200 s-1 to 3.75 s-1, allowing the spindle to rotate 10 times at each step before measurement. Data was then fitted to Power law model using Rheocalc® software to calculate flow (n) and consistency (K) indices (Brookfield Engineering, Middleboro, Mass.).

Yield Stress

Apparent yield stress ($\sigma_0$) of the samples was measured using model RV or HA fitted with vane attachment V-71 (Brookfield Engineering, Middleboro, Mass.) submerged to the secondary immersion mark. Model selection was based on the limits of measureable torque ranges for the units: 10% to 100%. The samples were pre-sheared at 20 RPM for 30 seconds, and then a zero torque step at 0.10 RPM was used to ensure a consistent start point for each, allowing torque values go to 0%. Samples were loaded into 118 ml vials that were 45 mm in diameter (item #0741-07, SKS Science). Test speeds (in RPM) were calculated so that the shear rates were as follows: 0.1 s-1 for samples ≤500 cP and 1.0 s-1 for samples >500 cP.

Processing

Pilot scale samples ranging from 10m to 15 kg were prepared in order to test the effect of commercial processing and to prepare enough samples for preliminary shelf life and sensory tests. Special care was taken to ensure the filling temperature did not go above 200° F. When the fill temperature was too high, seam from pockets of ultra-heated beverage caused the formation of foams that made continuous filling challenging. It also resulted in under-filling of the bottles and bottles collapse as the beverage cooled. Foams formed in this way were not stable and dissipated after several weeks of storage. The resulting products were clear.

Shelf Life Studies

Samples of the final prototype SWSL PRB-N-08 were prepared as described above and held under ambient conditions. Samples were pulled weekly for four weeks followed by monthly pulls.

Turbidity Measurements

The clarity (or cloudiness) of a liquid is measured by turbidity. The haziness of a fluid is generally caused by particles that are suspended in the liquid. In thin liquids, large particles generally settle, but in thickened beverages these particles are in a stable suspension and contribute to the cloudiness of the product. Turbidity was measured using a nephelometer that measures the amount of light that reaches a detector set perpendicular to the light source; the more turbid the fluid, the more particles present to scattering the source beam and the larger the reading by the detector. The units of turbidity from a calibrated nephelometer are called Nephelometric Turbidity Units (NTU).

A Hach 2100Q Portable Turbidimeter, silicon oil, lint-free soft cloth, and StablCal® standards were used. Before turbidity measurements, the instrument was calibrated using the StablCal® Standards (20, 100 and 800 NTU). An oiling cloth was used to clean the vials before measurements were taken. The sample cell was inserted into the cell compartment so the diamond or orientation mark aligns with the raised orientation mark in front of the cell compartment. After successful calibration, 15 ml of sample was carefully poured into the provided sample cell. The cell was capped and wiped clean with a lint free cloth to remove water spots and fingerprints. A thin film of silicon oil was applied to the cell to obtain an even film over the entire surface of the cell. The sample was gently inverted and inserted into the instrument cell compartment so the diamond orientation mark aligns with the raised orientation mark in the front of the cell compartment. The lid is closed and the "read" button on the instrument is pushed. Once the reading has stabilized the measurement was recorded.

Example 2

Exemplary Formulations

A. PRB-N.08

A high protein beverage formula was produced with a protein target of 10 g on 100 g of product and a 100 kilo calories target. For this formulation Xanthan gum was used as a thickening agent. Caramel color was added to resemble the color of typical hydrating beverages. A taste modulator (modulome) from Firmenich was added in order to mask the bitterness coming from the whey protein hydrolysate (WPH). Sodium Benzoate was added as post opening preservative, to prevent mold growth.

Materials and Methods

Reverse Osmosis (RO) Water
Ascorbic Acid
Sodium Potassium Meta Phosphate (Benephos)
Sodium Citrate
Cellulose Gum (CMC 2500)
Xanthan Gum (Keltrol T)
Whey Protein Hydrolysate (Arla Lacprodan HYDRO 365)
Citric Acid
Malic Acid
Sodium Benzoate
Sugar
Modulone
Phosphoric Acid (85%)
Caramel Color, P212
Nat Green Apple FLV WONF FAPG958

WPH was blended with water in a stainless-steel tank with constant agitation. Care was taken during the addition to prevent foaming from occurring due to over-blending.

Sodium Benzoate was added to the protein solution, followed by a dry blend of ascorbic acid, citric acid, malic acid and sodium citrate.

After the acids and salts were completely dissolved in the protein solution, the flavor/color blend was added to the protein solution. The pH was adjusted in steps with 85% phosphoric acid until the solution reached a pH=3.9. A blend of the xanthan/cellulose gum dispersed in sucrose was added to the protein solution with high shear mixing. Care was taken during the addition to prevent the formation of lumps and fisheyes. The resultant slurry was left to sit for 1-2 hrs to allow the gums to fully equilibrate and hydrate. The apparent viscosity was measured at a 30 s$^{-1}$ shear rate. If the apparent viscosity was below 1500 cP, it was adjusted by the stepwise addition of 0.01% w/w of additional gum blend. Between each step, the mixture was left to sit for 15 minutes before the viscosity was measured.

TABLE 1

PRB-N.08 (GMP Production)

| Ingredient | Supplier | % in formula |
|---|---|---|
| Xanthan Gum (Keltrol T Plus) | CP Kelco | 0.450% |
| Cellulose Gum (CMC 2500) | TIC Gums | 0.060% |
| Water | RO | 73.298% |
| Lacprodan | Arla | 6.600% |
| Ascorbic Acid | Latitude | 0.050% |
| Citric Acid | Tate & Lyle | 0.070% |
| Malic Acid | Tate & Lyle | 0.035% |
| Sodium Benzoate | Latitude | 0.025% |
| Sodium Citrate | Jungbunzlauer Inc | 0.040% |
| Sugar | Domino | 18.200% |
| Modulone 533934T | Firmenich | 0.150% |
| Phosphoric Acid (85%) | Brenntag North America | 0.660% |
| Caramel Color, P212 | Sethness | 0.013% |
| Nat Green Apple FLV WONF FAPG958 | Wild | 0.350% |
| Total | | 100.00% |

The resulting product was measured a day after production and it was inside suitable rheological parameters.

Samples of the final prototype SWSL PRB-N-08 were prepared using the reported procedure and held under ambient conditions. Samples were pulled weekly for four weeks followed by monthly pulls. After 35 days, the samples were found to be stable with no degradation in the viscosity.

B. PrB-H.08

A high protein beverage formula was produced with a protein target of 5 g on 100 g of product and a 100 kilo calories target. For this formulation Guar gum was used as the thickening agent. Caramel color was added to resemble the color of typical hydrating beverages. A taste modulator (modulome) from Firmenich was added to mask the bitterness coming from the WPH. Sodium Benzoate was added as post opening preservative, to prevent mold growth Materials and Methods
    Reverse Osmosis (RO) Water
    Ascorbic Acid
    Sodium Potassium Meta Phosphate (Benephos)
    Sodium Citrate
    Guar Gum
    Whey Protein Hydrolysate (Arla Lacprodan HYDRO 365)
    Citric Acid
    Malic Acid
    Sodium Benzoate
    Sugar
    Modulone
    Phosphoric Acid (85%)
    Caramel Color, P212
    Nat Green Apple FLV WONF FAPG958

WPH was blended with water in a stainless-steel tank with constant agitation. Care was taken during the addition to prevent foaming from occurring due to over-blending. Sodium Benzoate was added to the protein solution, followed by a dry blend of ascorbic acid, citric acid, malic acid and sodium citrate.

After the acids and salts were completely dissolved in the protein solution, the flavor/color blend was added to the protein solution. The pH was adjusted in steps with 85% phosphoric acid until the solution reached a pH=3.9. A blend of the xanthan/cellulose gum dispersed in sucrose was added to the protein solution with high shear mixing.

Care was taken during the addition to prevent the formation of lumps and fisheyes. The resultant slurry was left to sit for 1-2 hrs to allow the gums to fully equilibrate and hydrate. The apparent viscosity was measured at a 30 s$^{-1}$ shear rate. If the apparent viscosity was below 1500 cP, it was adjusted by the stepwise addition of 0.01% w/w of additional gum blend. Between each step, the mixture was left to sit for 15 minutes before the viscosity was measured.

TABLE 1

PRB-H.08 (GMP Production)

| Ingredient | Supplier | % in formula |
|---|---|---|
| Guar Gum | Dabisco | 0.910% |
| Water | RO | 72.598% |
| Lacprodan | Arla | 6.600% |
| Ascorbic Acid | Latitude | 0.050% |
| Citric Acid | Tate & Lyle | 0.070% |
| Malic Acid | Tate & Lyle | 0.035% |
| Sodium Benzoate | Latitude | 0.025% |
| Sodium Citrate | Jungbunzlauer Inc | 0.040% |
| Sugar | Domino | 18.500% |
| Modulone 533934T | Firmenich | 0.150% |
| Phosphoric Acid (85%) | Brenntag North America | 0.660% |
| Caramel Color, P212 | Sethness | 0.013% |
| Nat Green Apple FLV WONF FAPG958 | Wild | 0.350% |
| Total | | 100.00% |

C. PRB-H.09

A high protein beverage base formula was used to explore the effect of different proportions of the gums (Xanthan and CMC) that comprise the hydrocolloid system, on the rheological properties of the final product.

Materials and Methods
    Reverse Osmosis (RO) Water
    Ascorbic Acid
    Sodium Potassium Meta Phosphate (Benephos)
    Cellulose Gum (CMC 2500)
    Xanthan Gum (Keltrol T)
    Whey Protein Hydrolysate (Arla Lacprodan HYDRO 365)
    Citric Acid
    Malic Acid
    Sodium Benzoate
    Sugar
    Modulone
    Phosphoric Acid (85%)
    Caramel Color, P212
    Nat Apple Wonf 598682C WPH was blended with water in a stainless-steel tank with constant agitation. Care was taken during the addition to prevent foaming from occurring due to over-blending. Sodium Benzoate was added to the protein solution, followed by a dry blend of ascorbic acid, citric acid, malic acid and sodium citrate.

After the acids and salts were completely dissolved in the protein solution, the flavor/color blend was added to the protein solution. The pH was adjusted in steps with 85% phosphoric acid until the solution reached a pH=3.9. A blend of the xanthan/cellulose gum dispersed in sucrose was added to the protein solution with high shear mixing.

Care was taken during the addition to prevent the formation of lumps and fisheyes. The resultant slurry was left to sit for 1-2 hrs to allow the gums to fully equilibrate and hydrate. The apparent viscosity was measured at a 30 $s^{-1}$ shear rate. If the apparent viscosity was below 1500 cP, it was adjusted by the stepwise addition of 0.01% w/w of additional gum blend. Between each step, the mixture was left to sit for 15 minutes before the viscosity was measured.

TABLE 3

PRB-H.09 Benchtop Test of XN/CMC Blend

| Ingredient | Supplier | % in formula |
|---|---|---|
| Water | municipal | 72.078% |
| Lacprodan | Arla | 6.300% |
| Ascorbic Acid | DSM | 0.050% |
| Citric Acid | ADM | 0.070% |
| Malic Acid | Latitude | 0.035% |
| Sodium Benzoate | Jungbunzlauer Inc | 0.025% |
| Sugar | Domino | 18.700% |
| Modulone | Firmenich | 0.300% |
| Phosphoric Acid (85%) | Brenntag North America | 0.660% |
| Caramel Color, P212 | Sethness | 0.013% |
| Nat Apple Wonf 598682C | Firmenich | 0.270% |
| Xanthan Gum (Keltrol T) | CP Kelco | 0.400% |
| Cellulose Gum (CMC 2500) | TIC | 1.100% |

The resulting product was measured a day after production and it was inside the appropriate rheological parameters.

D. PRB-H.09 Lower Level of Gum

A high protein beverage base formula was formulated to explore the effect of different proportions of the gums (Xanthan and CMC) that comprise the hydrocolloid system, on the rheological properties of the final product.

Materials and Methods
  Reverse Osmosis (RO) Water
  Ascorbic Acid
  Sodium Potassium Meta Phosphate (Benephos)
  Cellulose Gum (CMC 2500)
  Xanthan Gum (Keltrol T)
  Whey Protein Hydrolysate (Aria Lacprodan HYDRO 365)
  Citric Acid
  Malic Acid
  Sodium Benzoate
  Sugar
  Modulone
  Phosphoric Acid (85%)
  Caramel Color, P212
  Nat Apple Wonf 598682C WPH was blended with water in a stainless-steel tank with constant agitation. Care was taken during the addition to prevent foaming from occurring due to over-blending. Sodium Benzoate was added to the protein solution, followed by a dry blend of ascorbic acid, citric acid, malic acid and sodium citrate.

After the acids and salts were completely dissolved in the protein solution, the flavor/color blend was added to the protein solution. The pH was adjusted in steps with 85% phosphoric acid until the solution reached a pH=3.9. A blend of the xanthan/cellulose gum dispersed in sucrose was added to the protein solution with high shear mixing.

Care was taken during the addition to prevent the formation of lumps and fisheyes. The resultant slurry was left to sit for 1-2 hrs to allow the gums to fully equilibrate and hydrate. The apparent viscosity was measured at a 30 $s^{-1}$ shear rate. If the apparent viscosity was below 1500 cP, it was adjusted by the stepwise addition of 0.01% w/w of additional gum blend. Between each step, the mixture was left to sit for 15 minutes before the viscosity was measured.

TABLE 4

PRB-H.09 Lower level of GUM (Benchtop TEST OF XN/CMC BLEND)

| Ingredient | Supplier | % in formula |
|---|---|---|
| Water | municipal | 72.458% |
| Lacprodan | Arla | 6.600% |
| Ascorbic Acid | DSM | 0.050% |
| Citric Acid | ADM | 0.070% |
| Malic Acid | Latitude | 0.035% |
| Sodium Benzoate | Jungbunzlauer Inc | 0.025% |
| Sugar | Domino | 18.200% |
| Modulone | Firmenich | 0.300% |
| Phosphoric Acid (85%) | Brenntag North America | 0.660% |
| Caramel Color, P212 | Sethness | 0.013% |
| Nat Apple Wonf 598682C | Firmenich | 0.350% |
| Xanthan Gum (Keltrol T) | CP Kelco | 0.330% |
| Cellulose Gum (CMC 2500) | TIC | 0.910% |

The resulting product was measured a day after production and it was inside the appropriate rheological parameters.

E. PRB-H.09 Lower Level of Gum Benchtop Test of XN/CMC Blend (2)

A high protein beverage base formula was formulated to explore the effect of different proportions of the gums (Xanthan and CMC) that comprise the hydrocolloid system, on the rheological properties of the final product.

Materials and Methods
  Reverse Osmosis (RO) Water
  Ascorbic Acid
  Sodium Potassium Meta Phosphate (Benephos)
  Cellulose Gum (CMC 2500)
  Xanthan Gum (Keltrol T)
  Whey Protein Hydrolysate (Aria Lacprodan HYDRO 365)
  Citric Acid
  Malic Acid
  Sodium Benzoate
  Sugar
  Modulone
  Phosphoric Acid (85%)
  Caramel Color, P212
  Nat Apple Wonf 598682C WPH was blended with water in a stainless-steel tank with constant agitation. Care was taken during the addition to prevent foaming from occurring due to over-blending. Sodium Benzoate was added to the protein solution, followed by a dry blend of ascorbic acid, citric acid, malic acid and sodium citrate.

After the acids and salts were completely dissolved in the protein solution, the flavor/color blend was added to the protein solution. The pH was adjusted in steps with 85% phosphoric acid until the solution reached a pH=3.9. A blend of the xanthan/cellulose gum dispersed in sucrose was added to the protein solution with high shear mixing.

Care was taken during the addition to prevent the formation of lumps and fisheyes. The resultant slurry was left to sit for 1-2 hrs to allow the gums to fully equilibrate and hydrate. The apparent viscosity was measured at a 30 s$^{-1}$ shear rate. If the apparent viscosity was below 1500 cP, it was adjusted by the stepwise addition of 0.01% w/w of additional gum blend. Between each step, the mixture was left to sit for 15 minutes before the viscosity was measured.

TABLE 5

PRB-H.09 Lower Level of Gum Benchtop Test of XN/CMC Blend (2)

| Ingredient | Supplier | % in formula |
|---|---|---|
| Water | municipal | 72.578% |
| Lacprodan | Arla | 6.600% |
| Apple Essence 050001 | FruitSmart | 0.000% |
| Citric Acid | ADM | 0.070% |
| Malic Acid | Latitude | 0.035% |
| Sodium Benzoate | Jungbunzlauer Inc | 0.025% |
| Sugar | Domino | 18.200% |
| Modulone | Firmenich | 0.300% |
| Phosphoric Acid (85%) | Brenntag North America | 0.660% |
| Caramel Color, P212 | Sethness | 0.013% |
| Nat Apple Wonf 598682C | Firmenich | 0.350% |
| Xanthan Gum (Keltrol T) | CP Kelco | 0.300% |
| Cellulose Gum (CMC 2500) | TIC | 0.820% |

The resulting product was measured a day after production and it was inside the appropriate rheological parameters.

Example 3

Alcohol-Containing Beverages

Beverages comprising alcohol were prepared as described above. Tables 6-8 show components of beverages comprising 2-5% alcohol by weight. All of the formulations tested comprised 100 kcal and 5 g of protein per 100 g of beverage. Samples were heated to 195° F. in a microwave. A 300 g batch of each formulation was prepared.

TABLE 6

Cranberry 2% alcohol by weight (ABW)

| Ingredient | Supplier | % in formula | g per batch |
|---|---|---|---|
| Xanthan Gum (Keltrol T Plus) | CP Kelco | 0.380% | 1.1 |
| Cellulose Gum (CMC 2500) | TIC | 0.060% | 0.2 |
| Everclear 95% | | 2.105% | 6.3 |
| Water | RO | 71.347% | 214.0 |
| Lacprodan | Arla | 6.500% | 19.5 |
| Sugar | Domino | 18.000% | 54.0 |
| Sodium Benzoate | KIC Chemicals | 0.025% | 0.1 |
| Cranberry Type Flavor, Nat 839.0211U | FONA | 0.250% | 0.8 |
| Exberry Valencia Red 154215 | GNT | 0.300% | 0.9 |
| Citric Acid | | 0.200% | 0.6 |
| Phosphoric Acid (75%)* | Innophos | 0.83% | 2.5 |
| Total | | 100.000% | 300.00 |

TABLE 7

Cranberry 3% ABW

| Ingredient | Supplier | % in formula | g per batch |
|---|---|---|---|
| Xanthan Gum (Keltrol T Plus) | CP Kelco | 0.380% | 1.1 |
| Cellulose Gum (CMC 2500) | TIC | 0.060% | 0.2 |
| Everclear 95% | | 3.158% | 9.5 |
| Water | RO | 70.294% | 210.9 |
| Lacprodan | Arla | 6.500% | 19.5 |
| Sugar | Domino | 18.000% | 54.0 |
| Sodium Benzoate | KIC Chemicals | 0.025% | 0.1 |
| Cranberry Type Flavor, Nat 839.0211U | FONA | 0.250% | 0.8 |
| Exberry Valencia Red 154215 | GNT | 0.300% | 0.9 |
| Citric Acid | | 0.200% | 0.6 |
| Phosphoric Acid (75%)* | Innophos | 0.83% | 2.5 |
| Total | | 100.000% | 300.00 |

TABLE 8

Cranberry 5% ABW

| Ingredient | Supplier | % in formula | g per batch |
|---|---|---|---|
| Xanthan Gum (Keltrol T Plus) | CP Kelco | 0.380% | 1.1 |
| Cellulose Gum (CMC 2500) | TIC | 0.060% | 0.2 |
| Everclear 95% | | 5.263% | 15.8 |
| Water | RO | 68.189% | 204.6 |
| Lacprodan | Arla | 6.500% | 19.5 |
| Sugar | Domino | 18.000% | 54.0 |
| Sodium Benzoate | KIC Chemicals | 0.025% | 0.1 |
| Cranberry Type Flavor, Nat 839.0211U | FONA | 0.250% | 0.8 |
| Exberry Valencia Red 154215 | GNT | 0.300% | 0.9 |
| Citric Acid | | 0.200% | 0.6 |
| Phosphoric Acid (75%)* | Innophos | 0.83% | 2.5 |
| Total | | 100.000% | 300.00 |

Table 9 shows the results of physical parameters for the thickened alcohol-containing beverages described in Tables 6-8. The results show that the beverages meet one or more of the parameters for pH, viscosity, and turbidity described herein.

TABLE 9

Physical parameters of alcohol-containing beverages.

| Category | Sample | pH | Viscosity (cP) | Turbidity (NTU) |
|---|---|---|---|---|
| Alcohol | Cranberry 2% ABW | 3.88 | 363.8 | 837 |
| | Heated | 3.9 | 373.1 | 556 |
| Alcohol | Cranberry 3% ABW | 3.85 | 366.9 | 559 |
| | Heated | 3.87 | 370 | 638 |
| Alcohol | Cranberry 5% ABW | 3.94 | 342.1 | overrange |
| | Heated | 3.96 | 377.7 | overrange |

Example 4

Freeze-Thaw

This example describes freeze-thaw experiments of exemplary beverages demonstrating that a thawed sample maintains desirable properties. Tables 10-12 show components of beverages. Table 13 shows that viscosity and turbidity of exemplary beverages are the same before freezing and after thawing.

TABLE 10

Iced tea

| Ingredient | Supplier | % in formula | g per batch |
|---|---|---|---|
| Xanthan Gum (Keltrol T Plus) | CP Kelco | 0.380% | 91.2 |
| Cellulose Gum (CMC 2500) | TIC | 0.060% | 14.4 |
| Water | Supplier | 73.425% | 17,622.0 |
| Lacprodan | Arla | 6.500% | 1,560.0 |
| Sugar | Domino | 18.000% | 4,320.0 |
| Sodium Benzoate | KIC Chemicals | 0.025% | 6.0 |
| Black Tea Treattarome Iced 9765 | Treatt | 0.210% | 50.4 |
| Kiwifruit Treattarome 9770 | Treatt | 0.150% | 36.0 |
| Exberry Rustic Brown 931804 | GNT | 0.250% | 60.0 |
| Phosphoric Acid (75%)* | Innophos | 1.00% | 240 |
| Total | | 100.000% | 24,000.00 |

TABLE 11

Lemonade

| Ingredient | Supplier | % in formula | g per batch |
|---|---|---|---|
| Xanthan Gum (Keltrol T Plus) | CP Kelco | 0.380% | 45.6 |
| Cellulose Gum (CMC 2500) | TIC | 0.060% | 7.2 |
| Water | RO | 72.105% | 8,652.6 |
| Lacprodan | Arla | 6.500% | 780.0 |
| Sugar | Domino | 18.000% | 2,160.0 |
| Cyclic Cluster Dextrin | Glico | 1.000% | 120.0 |
| Sodium Benzoate | KIC Chemicals | 0.025% | 3.0 |
| Natural Raspberry Type Flavor 188a132 | Abelei | 0.200% | 24.0 |
| Natural Lemonade Type Flavor 160a164 | Abelei | 0.300% | 36.0 |
| Natural Meyer Lemon Type Flavor WONF 160a155 | Abelei | 0.200% | 24.0 |
| Exberry Royal Pink 804140 | GNT | 0.030% | 3.6 |
| Citric Acid | | 0.200% | 24.0 |
| Phosphoric Acid (75%)* | Innophos | 1.00% | 120 |
| Total | | 100.000% | 12,000.00 |

TABLE 12

Cranberry

| Ingredient | Supplier | % in formula | g per batch |
|---|---|---|---|
| Xanthan Gum (Keltrol T Plus) | CP Kelco | 0.380% | 91.2 |
| Cellulose Gum (CMC 2500) | TIC | 0.060% | 14.4 |
| Water | RO | 73.285% | 17,588.4 |
| Lacprodan | Arla | 6.500% | 1,560.0 |
| Sugar | Domino | 18.000% | 4,320.0 |
| Sodium Benzoate | KIC Chemicals | 0.025% | 6.0 |
| Cranberry Type Flavor, Nat 839.0211U | FONA | 0.250% | 60.0 |
| Exberry Valencia Red 154215 | GNT | 0.300% | 72.0 |
| Citric Acid | | 0.200% | 48.0 |
| Phosphoric Acid (75%)* | Innophos | 1.00% | 240 |
| Total | | 100.000% | 24,000.00 |

TABLE 13

Freeze-thaw data

| Category | Sample | pH | Viscosity (cP) | Turbidity (NTU) |
|---|---|---|---|---|
| Frozen | PrB-N.13 Cranberry | 3.87 | 277.1 | 258 |
| | Thawed | 3.93 | 272.4 | 249 |
| Frozen | PrB-N.13 Iced Tea | 3.9 | 298.8 | 31.1 |
| | Thawed | 3.95 | 292.6 | 58.4 |
| Frozen | PrB-N.13 Lemonade | 3.95 | 298.8 | 63.1 |
| | Thawed | 4 | 286.4 | 75.8 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A beverage, comprising:
2 to 10 g of complete protein per 100 mL serving, wherein said beverage has an apparent viscosity between 50 cp and 2000 cp and is clear having a turbidity reading from 0 to 1000 NTUs.

2. The beverage of claim 1, wherein said beverage is ready to drink.

3. The beverage of claim 1, wherein said beverage has approximately 100 kcals of energy per 100 mL of beverage.

4. The beverage of claim 1, wherein said beverage comprises xanthan gum, cellulose gum, whey protein hydrolysate, ascorbic acid, citric acid, malic acid, sodium benzoate, sodium citrate, sugar, phosphoric acid, and water.

5. The beverage of claim 4, wherein said whey protein hydrolysate is present at a concentration of 6% to 7% w/w.

6. The beverage of claim 5, wherein said hydrolysate is present at a concentration of 6.6% w/w.

7. The beverage of claim 5, wherein said hydrolysate is present at a concentration of 6.3% w/w.

8. The beverage of claim 1, wherein said beverage further comprises one or more additional agents selected from the group consisting of one or more gums, a sweetener, an acid, a preservative, and one or more coloring or flavoring agents.

9. The beverage of claim 8, wherein said gum is cellulose gum and/or xanthan gum.

10. The beverage of claim 1, wherein said beverage comprises water, whey protein hydrolysate, flavoring, coloring, citric acid, malic acid, sodium benzoate, sugar, phosphoric acid, xanthan gum, and cellulose gum.

11. The beverage of claim 10, wherein said beverage comprises 72.6% water, 6.6% whey protein hydrolysate, 0.65% flavoring, 0.13% coloring, 0.07% citric acid, 0.035% malic acid, 0.025% sodium benzoate, 18.2% sugar, 0.66% phosphoric acid, 0.3% xanthan gum, and 0.82% cellulose gum.

12. The beverage of claim 10, wherein said beverage further comprises 0.05% ascorbic acid.

13. The beverage of claim 1, wherein said beverage comprises guar gum, water, whey protein hydrolysate, ascorbic acid, flavoring, coloring, citric acid, malic acid, sodium benzoate, sodium citrate, sugar, and phosphoric acid.

14. The beverage of claim 13, wherein said beverage comprises 0.91% guar gum, 72.6% water, 6.6% whey protein hydrolysate, 0.05% ascorbic acid, 0.5% flavoring, 0.013% coloring, 0.07% citric acid, 0.035% malic acid, 0.025% sodium benzoate, 0.04% sodium citrate, 18.5% sugar, and 0.66% phosphoric acid.

15. The beverage of claim 12, wherein said beverage further comprises 0.04% sodium citrate.

16. The beverage of claim 1, wherein said beverage further comprises one or more additional components selected from the group consisting of ethanol, medical grade marijuana, a marijuana extract, and a synthetic cannabinoid.

17. The beverage of claim 1, wherein said beverage is frozen.

18. A method, comprising:
   administering the beverage of claim 1 to a subject.

* * * * *